: US006328855B1

United States Patent
Bischof et al.

(10) Patent No.: US 6,328,855 B1
(45) Date of Patent: Dec. 11, 2001

(54) METHOD FOR PRODUCING (+)-EXO-6-PHENYL-3-AZABICYCLO-[3.2.0]HEPTANES

(75) Inventors: Norbert Bischof, Mannheim; Ernst Buschmann, Ludwigshafen; Michael Henningsen, Frankenthal; Georg Arnold Krei, Altrip; Rainer Munschauer, Shrewsbury; Thomas Pfeiffer, Böhl-Iggelheim; Gerd Steiner, Kirchheim; Wolfgang Viergutz, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/807,218

(22) PCT Filed: Oct. 13, 1999

(86) PCT No.: PCT/EP99/07682

§ 371 Date: Apr. 11, 2001

§ 102(e) Date: Apr. 11, 2001

(87) PCT Pub. No.: WO00/23423

PCT Pub. Date: Apr. 27, 2000

(30) Foreign Application Priority Data

Oct. 21, 1998 (DE) .............................. 198 48 521

(51) Int. Cl.[7] .................................................. C07D 209/52
(52) U.S. Cl. ................ 204/162; 204/157.82; 204/157.86
(58) Field of Search ....................... 548/452; 204/157.81, 204/157.82, 157.86

(56) References Cited

U.S. PATENT DOCUMENTS 5,521,209 * 5/1996 Steiner et al. .................... 514/112

5,703,091 * 12/1997 Steiner et al. .................... 514/300

* cited by examiner

Primary Examiner—Floyd D. Higel
Assistant Examiner—Golam M. M. Shameem
(74) Attorney, Agent, or Firm—Keil & Weinkauf

(57) ABSTRACT

A process for preparing (+)-exo-6-phenyl-3-azabicyclo [3.2.0]heptanes of the formula I

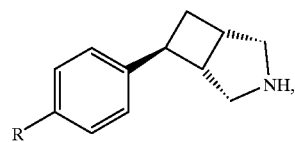

where R is hydrogen, chlorine, bromine, fluorine or methoxy, which comprises photocyclizing a bisallylammonium salt of the formula II

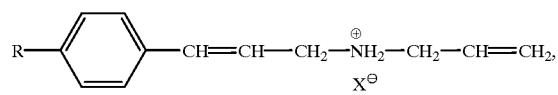

where R has the meanings given above and $X^-$ is an anion, in an inert solvent in a glass apparatus with addition of sensitizer and precipitating using (−)-ditoluoyltartaric acid the desired (+)-exo-isomer I as ditoluoyltartrate from the resulting mixture, with or without recrystallization of this tartrate from an alcohol/water mixture.

5 Claims, No Drawings

METHOD FOR PRODUCING (+)-EXO-6-PHENYL-3-AZABICYCLO-[3.2.0]HEPTANES

This application is a 371 of PCT/EP 99/07682 Oct. 13, 1999.

The invention relates to a simple process which is technically easy to carry out for preparing (+)-exo-6-phenyl-3-azabicyclo[3.2.0]heptanes. These compounds have importance as precursors for neuroleptics (DE 4219973, 4427647, 4427648).

6-Phenyl-3-azabicyclo[3.2.0]heptanes may be synthesized by photolytic cyclization of bisallylammonium salts 1. In the photocyclization, four stereoisomers 2 are produced (diagram 1).

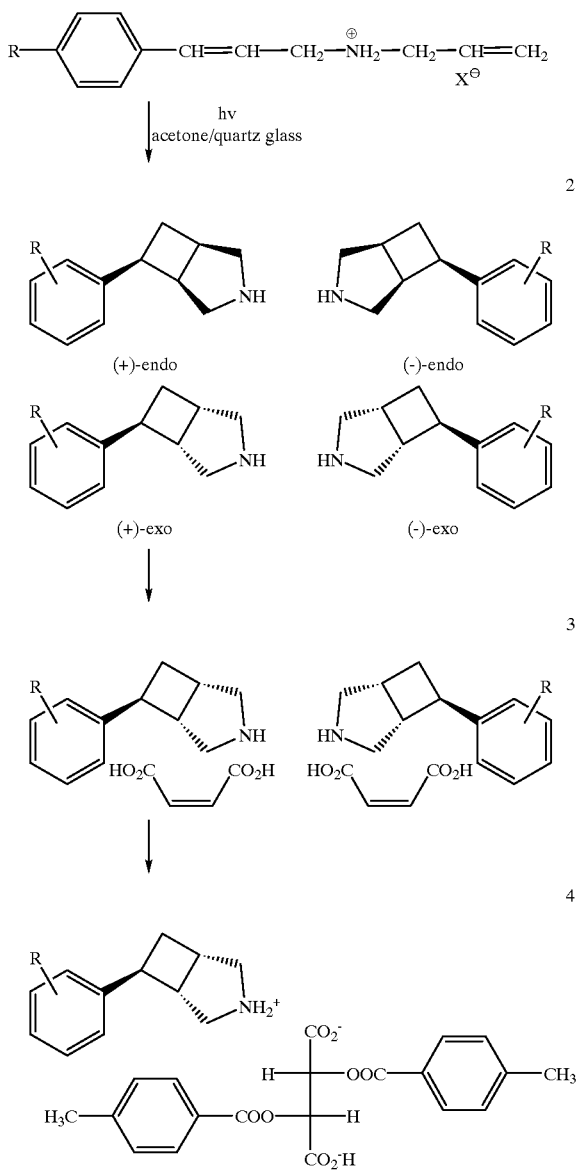

The unwanted endo isomers are separated off by a maleate recipitation to form 3, then the (+)-exo isomers are isolated as ditoluoyltartrate 4 (Heterocycles 40 (1995) 319). On a laboratory scale, the process can very readily be carried out to prepare pure 6-phenyl-3-azabicyclo[3.2.0]heptanes. However, in the industrial preparation there are serious problems:

Fractionating the isomer mixture 2 requires the multiplicity of process steps:

Neutralization of the crude solution from the photocyclization;

Extraction of the isomer mixture with ether;

Drying the solution over $Na_2SO_4$;

Filtering off the $Na_2SO_4$;

Concentrating the solution;

Dissolving the residue in isopropanol;

Precipitating the maleate with maleic acid;

Filtering off the maleate;

Suspending the maleate in water and adding alkali;

Extraction of the exo-amine with ether;

Evaporating the solvent;

Dissolving the exo-isomers in ethanol;

Precipitating the ditoluoyltartrate with (−)-ditoluoyltartaric acid; and

Recrystallization of the ditoluoyltartrate from propanol/water.

This synthesis produces large amounts of residues which must be disposed of. In addition, the photocyclization must be performed in a quartz apparatus. However, in particular large quartz apparatuses are difficult to produce, highly fragile and can only be repaired with great technical effort.

When the laboratory method is converted to the industrial scale, furthermore, interfering deposits occur on the quartz light source. The reaction is slowed down by this and in many cases is incomplete.

To precipitate the ditoluoyltartrate 4, a salt consisting of one equivalent each of (−)-ditoluoyltartaric acid (=DTT) and 6-phenyl-3-azabicycloheptane, the expensive (−)-ditoluoyltartaric acid is used in excess at 130%. This also produces large amounts of expensive residue here.

In the concluding recrystallization of 4 from propanol/water, during the longer heat-up and cool-down times in the industrial operation of large stirred tanks, partial decomposition of the ditoluoyltartrate 4 occurs, so that the yields found in the laboratory are not achieved.

It is an object of the present invention to solve the problems which occur when the laboratory synthesis is converted to an industrial scale.

We have found that this object is achieved by a process for preparing (+)-exo-6-phenyl-3-azabicyclo[3.2.0]heptanes of the formula I

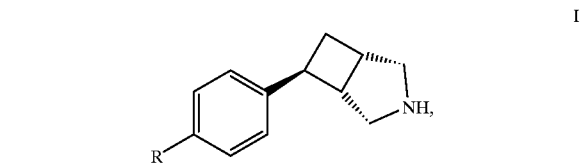

where R is hydrogen, chlorine, bromine, fluorine or methoxy, which comprises photocyclizing a bisallylammonium salt of the formula II

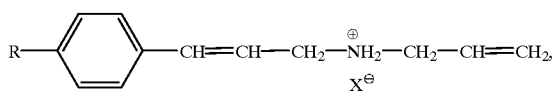

where R has the meanings given above and X⁻ is an anion, in an inert solvent in a glass apparatus with addition of sensitizer and precipitating using (−)-ditoluoyltartaric acid the desired (+)-exo-isomer I as ditoluoyltartrate from the resulting mixture, with or without recrystallization of this tartrate from an alcohol/water mixture, X⁻ is halide, sulfate, phosphate, nitrate or another suitable anion; preference is given to chloride and phosphate.

The reaction takes place in an inert solvent such as water, an alcohol such as methanol, ethanol, propanol, a ketone such as acetone, methyl ethyl ketone, or an amide such as dimethylformamide or N-methylpyrrolidone; preference is given to acetone.

Expediently, the photocyclization is carried out with addition of a sensitizer such as benzophenone, acetophenone, benzophenones having substituents on the aromatic moiety, or acetophenones (preferably acetophenone), at temperatures of from 0 to 80° C., in particular at from 15 to 30° C. Expediently, the photocyclization takes place in a glass apparatus. Suitable light sources are high-pressure mercury lamps or comparable light sources.

Just as in the cyclization in quartz apparatuses disclosed in the literature, isomer mixtures are obtained in which the compounds I are present at about 45%. The remainder consists of about 45% of the (−)-exo isomers and about 5% of each of the (+)- and (−)-endo isomers formed.

The (+)-exo-6-phenyl-3-azabicyclo[3.2.0]heptane produced by the novel process may be precipitated directly from the crude photocyclization mixture using (−)-ditoluoyltartaric acid (=DTT). The (−)-exo enantiomer and the endo stereoisomers surprisingly remain in solution in this case. The novel process for separating off the desired (+)-exo isomers thus consists of only a few process steps. There are no time-consuming extraction steps.

Little is known of the photocyclization of bisallylamines (Heterocycles 40, (1995) 319) and the references cited there). Surprisingly, it has been found that the photocyclization can also be carried out in simple glass apparatuses if a suitable sensitizer, e.g. preferably a triplet sensitizer, is added. Acetophenone is a particularly good sensitizer. In the glass apparatuses there is then no interfering deposit formation on the light source.

It has further been found that the DTT amount may be reduced from 130% to from 20 to 30 mol %, based on crude bicycloheptane used. Instead of the salts which consist of one equivalent of bicycloheptane and one equivalent of DTT, salts are precipitated out which consist of one equivalent of DTT and two equivalents of bicycloheptane. The yields and purities of the desired stereoisomer I remain unchanged here.

After completion of the photocyclization, if the photocyclization solvent was not an alcohol, a solvent exchange is performed, that is to say the solvent used is evaporated off and replaced by a suitable alcohol, such as methanol, ethanol, n-propanol, isopropanol, n-butanol, sec-butanol, isobutanol, n-pentanol or by an alcohol mixture. The preferred solvent is ethanol. Water is then added and a pH of from 6.5 to 7.5, preferably 7, is set using a suitable base, such as NaOH, KOH, $Na_2CO_3$, $K_2CO_3$ or amines such as ammonia, diethylamine or triethylamine. Preference is given to triethylamine.

Then, using an alcoholic (preferably ethanolic) solution of (−)-ditoluoyltartaric acid, the desired (+)-exo enantiomer of the formula III is precipitated from the crude solution as ditoluoyltartrate

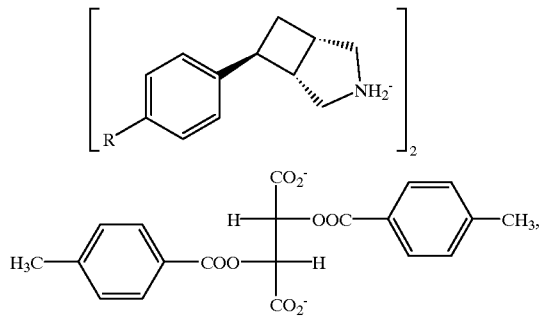

one equivalent of DTT crystallizing out with each two equivalents of the bicyclic amine. The best yields and product purities are obtained if use is made of from 20 to 35 mol % of (−)-DTT, based on isomer mixture of I used. Preference is given to 20–35 mol %. The bicyclic amines are obtained as ditoluoyltartrates III in a chemical purity of >99% and optical purities of >96% as (+)-exo isomers.

To further improve the optical purity, these salts can be recrystallized.

Suitable solvents for the recrystallization are optimally alcohol/water mixtures. Preferably, propanol/water mixtures are used. The recrystallization achieves excellent chemical and optical purities (in each case >99.5%).

If a small amount (approximately from 1 to 5% of the total amount) of a tertiary amine, preferably triethylamine, is added during the recrystallization, this avoids the decomposition of the ditoluoyltartrate III during the long heat-up and cool-down times in the larger pilot plant apparatuses.

The example below illustrates the invention.

EXAMPLE 1 a) Photocyclization 335.7 kg of N-allyl-N-[3-(4-fluorophenyl)allyl]amine . $H_3PO_4$ (IIa) were suspended in 225.6 kg of acetophenone and 4300 l of acetone. After adding 71.7 kg of phosphoric acid (85% pure) and 609.6 l of water, a homogeneous solution was formed which after irradiation for 5 days with a 40 kW high-pressure mercury lamp was completely reacted. A stereoisomer mixture of 6-(4-fluorophenyl)-3-azabicyclo[3.2.0]heptane had formed.

The ratio of exo:endo isomer was from 90.6:9.4 to 95.8:4.2.

b) Racemate separation using (−)-ditoluoyltartaric acid

The photocyclization product obtained according to a) was heated to reflux. Acetone was then distilled off until an internal temperature of 60° C. had been achieved. 680 l of ethanol and 470 l of water were added and the pH was adjusted to 7 using triethylamine. At 40° C., 490.8 kg of a 25% strength ethanolic solution of (−)-ditoluoyltartaric acid were added. The solution was cooled to −5° C. and the solid (IIIa) was centrifuged off. The solid remaining in the centrifuge was washed with a mixture of 250 l of water and 250 l of ethanol. The product was dried in a vacuum drying cabinet at 50° C. Yield: 145 kg of ditoluoyltartrate (65%), optical purity: 97.3%, chemical purity: 99.3%.

c) Recrystallization of the tartrate 225 kg of the ditoluoyltartrate (IIIa) were heated to reflux in 1020 l of n-propanol, 1020 l of water and 144 l of triethylamine. The mixture was cooled to −5° C. and the product was separated off by a centrifuge. After drying in a vacuum drying cabinet at 50° C., 175.8 kg of (+)-exo-6-phenyl-3-azabicyclo[3.2.0]heptanes (78.4%) were obtained. Chemical purity: 99.8%, optical purity: 99.8%.

We claim:

1. A process for preparing (+)-exo-6-phenyl-3-azabicyclo[3.2.0]heptanes of the formula I

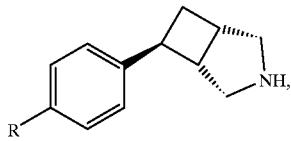

I where R is hydrogen, chlorine, bromine, fluorine or methoxy, which comprises photocyclizing a bisallylammonium salt of the formula II

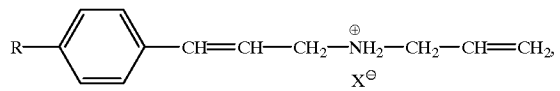

II where R has the meanings given above and $X^-$ is an anion, in an inert solvent in a glass apparatus with addition of sensitizer and precipitating using (−)-ditoluoyltartaric acid the desired (+)-exo-isomer I as ditoluoyltartrate from the resulting mixture, with or without recrystallization of this tartrate from an alcohol/water mixture.

2. A process as claimed in claim 1, wherein the sensitizer used is acetophenone.

3. A process as claimed in claim 1, wherein ethanol or n-propanol is used for the precipitation and recrystallization.

4. A process as claimed in claim 1, wherein, in the recrystallization of the ditoluoyltartrate, a tertiary amine is added.

5. A ditoluoyltartrate of the formula III

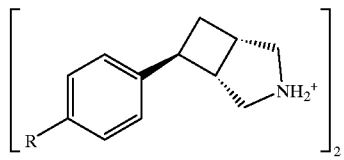

III

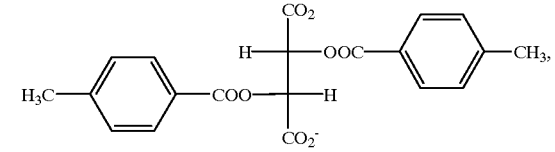

where R has the meaning specified in claim 1.

* * * * *